United States Patent [19]

Albright et al.

[11] 3,987,114
[45] Oct. 19, 1976

[54] PROCESS FOR PRODUCING PHENOLIC COMPOUNDS FROM COAL

[75] Inventors: Charles W. Albright, South Charleston; Hubert G. Davis, Charleston, both of W. Va.

[73] Assignee: Union Carbide Corporation, New York, N.Y.

[22] Filed: June 5, 1969

[21] Appl. No.: 830,839

Related U.S. Application Data

[63] Continuation-in-part of Ser. No. 376,415, June 19, 1964, abandoned.

[52] U.S. Cl. .......................... 260/627 H; 260/621 R
[51] Int. Cl.² ..................... C07C 39/02; C07C 37/22
[58] Field of Search ............ 260/627 R, 627 H, 621, 260/376, 415; 208/10, 8

[56] References Cited
UNITED STATES PATENTS

| | | | |
|---|---|---|---|
| 1,820,908 | 9/1931 | Cross | 260/627 H |
| 3,105,095 | 9/1963 | Oshima et al. | 260/627 H |
| 3,231,486 | 1/1966 | Perry et al. | 260/627 H |
| 3,321,393 | 5/1967 | Schuman et al. | 208/10 |

*Primary Examiner*—James O. Thomas, Jr.
*Assistant Examiner*—W. B. Lone
*Attorney, Agent, or Firm*—Israel Blum

[57] ABSTRACT

A liquid product containing a high percentage of phenolic compounds is obtained from coal by the hydrocarbonization of coal in a fluidizing bed in the presence of hydrogen. The hydrocarbonization is conducted at a temperature of 480°-600° C. and a hydrogen partial pressure of from about 100 to about 1,200 psi and an average solids residence time of 1 to about 30 minutes. Oxidation of the coal even by atmospheric air must be substantially avoided to maximize phenolic production. Oxidizing coal reduces the tar and the phenolic yield by as much as 50 percent in some instances. Subbituminous, especially non-agglomerating varieties are especially preferred coals.

6 Claims, 1 Drawing Figure

U.S. Patent    Oct. 19, 1976    3,987,114

Figure 1:
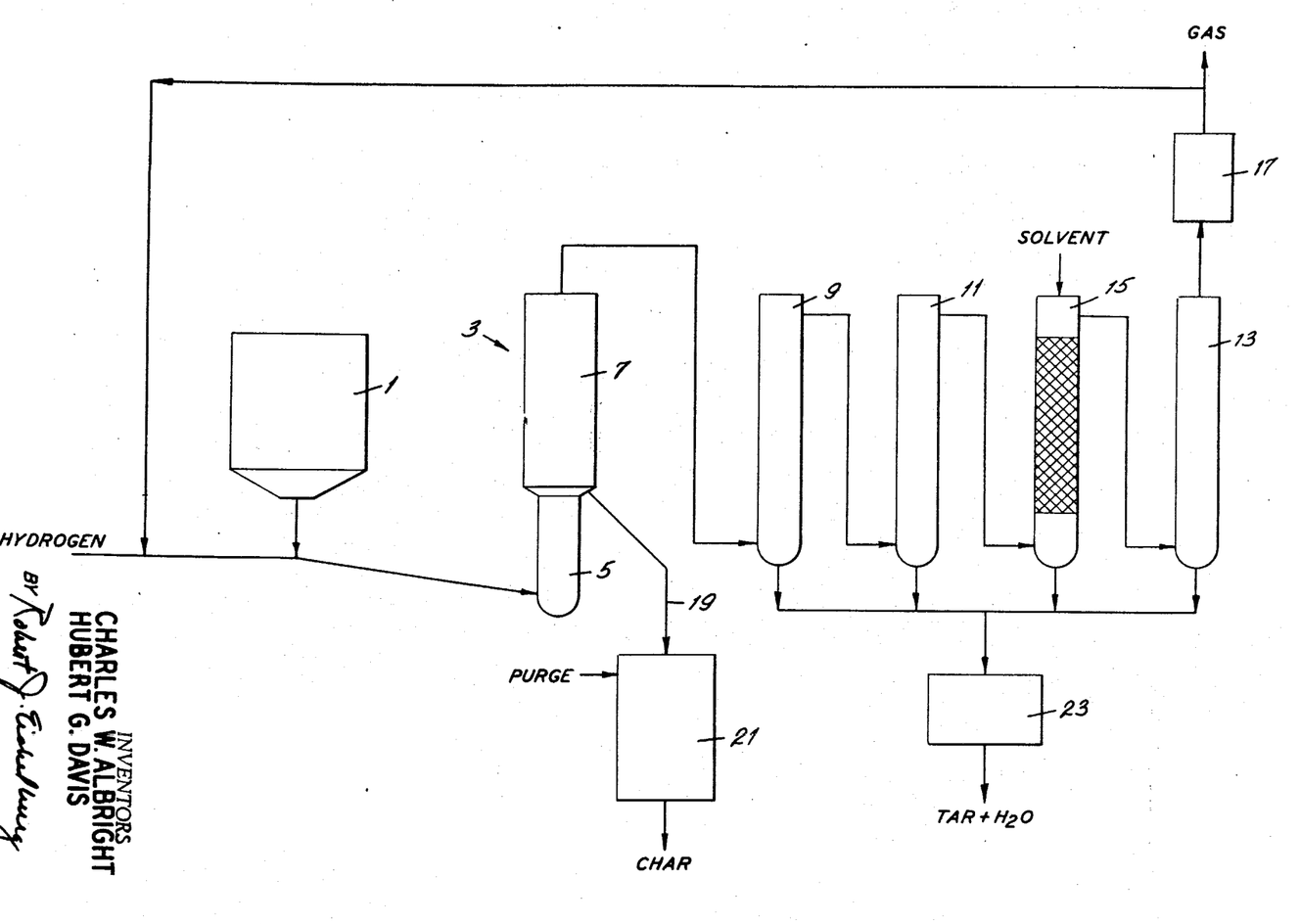

INVENTORS
CHARLES W. ALBRIGHT
HUBERT G. DAVIS
BY Robert J. Eichelberg
ATTORNEY

PROCESS FOR PRODUCING PHENOLIC COMPOUNDS FROM COAL

The present application is a continuation-in-part application of U.S. Pat. application Ser. No. 376,415, filed June 19, 1964 and now abandoned.

This invention relates generally to a process for the production of phenolic compounds from coal. More particularly, this invention concerns a method for reacting coal with hydrogen in a manner such that the ratio of phenolic compounds produced to hydrogen consumed is maximized.

Coal is known to be a potentially valuable source of chemical compounds, and considerable effort has been expended in an attempt to develop a process for the efficient production of such chemicals. The first processes involved the carbonization of coal in an inert atmosphere to produce only about 10 to 15 weight per cent, based on the coal charged, of a liquid product and about 70 to 75 weight per cent of a solid char. Since these products were generally suitable only as fuels, these processes were not commercially feasible in this country.

In an effort to convert the bulk of the coal to a liquid product, the hydrogenolysis processes were developed. In these processes a slurry of coal and usually a catalyst in oil was heated in the presence of hydrogen gas at 450° to 550° C. and 5000 to 10,000 psig. Although these processes were successful in that the amount of liquid product was substantially increased, they were not commercially acceptable because the hydrogen requirements were too high in comparison with the value of the products obtained.

More recently, dry "hydrocarbonization" processes were developed wherein coal was heated with hydrogen gas. However, these processes were generally batch-type processes and, because they were conducted at greatly elevated temperatures and pressures, resulted in the production of hydrocarbon gases and liquids useful mainly as fuels.

The process of this invention is an improved hydrocarbonization process wherein the primary product, amounting up to about 5 to 10 weight per cent of the coal charged, consists of valuable phenolic compounds. In addition, the ratio of phenolic compounds and other liquid products to the amount of hydrogen consumed is considerably higher than that of the prior art processes, resulting, for the first time, in an economically attractive method for obtaining chemicals, particularly phenolic compounds, from coal. In addition, the amount of char is reduced from 70 to 75 per cent to less than 60 per cent, and often as low as 30 per cent of the coal charged.

The process of this invention, in its broadest aspect, comprises continuously feeding particulate coal and a hydrogen-containing, oxygen-free gas to a hydrocarbonization zone, maintaining the coal in a fluidized state in said hydrocarbonization zone under relatively mild conditions of temperature and pressure to convert said coal to a vapor and a solid char, and continuously withdrawing the vapors and char from the hydrocarbonization zone. In this process there is a continuous movement of the solids in the fluidized bed throughout the hydrocarbonization zone, with the composition of the solids in the bed approximating that of the char.

The hydrocarbonization zone is maintained at an average temperature of from about 480° C. to about 600° C. by known heating methods. Although any convenient source of heat can be employed, it has been found that, when the feed coal is preheated in the range of about 250° C. to about 300° C., the exothermic heat of reaction in the hydrocarbonization zone is sufficient to maintain the desired reaction temperature. Although temperatures of less than 480° C. can be employed, they are generally not desirable because the rate of reaction of coal with hydrogen is too slow for a practical process. The temperature must not exceed about 600° C., however, for at these more elevated temperatures the oxygen present in the coal, instead of appearing in the product in the form of phenolic compounds, is converted to water, carbon monoxide and carbon dioxide. Temperatures in the range of 520° C to 580° C. are preferred.

The gas employed can be pure hydrogen or hydrogen in admixture with an inert gas such as nitrogen or the like. However, the hydrogen partial pressure in the hydrocarbonization zone should be between about 100 psi to about 1200 psi. At partial pressures of less than 100 psi the rate of reaction with the coal is too slow, and at partial pressures of greater than 1200 psi the amount of hydrogen consumed is too great for an economical process. Hydrogen partial pressures of from about 300 to about 500 psi are preferred. By the term "hydrogen partial pressure", as employed in the specification and claims, is meant the log mean average of the hydrogen partial pressure in the feed and product gas streams.

In another aspect falling within the broad scope of the present invention it has been discovered that in order to maximize the production of phenolic materials from coal, non-oxidizing conditions or substantially non-oxidizing conditions must be employed in all phases of the operation such as during the mining, shipping, storage, preparation and reaction of the coal employed especially where the bituminous coals are used such as sub-bituminous coals particularly those of the non-agglomerating types especially types such as sub-bituminous C and lower ranked coals such as lignitic coals.

Coals have been classified according to rank as noted in the following table, Table A.

TABLE A

Classification of Coals by Rank.[a]
(Legend: F.C. = fixed carbon; V.M. = volatile matter; B.t.u. = British thermal units)

| Class | Group | Limits of fixed carbon or B.t.u., ash free basis |
|---|---|---|
| I. Anthracite | 1. Meta-anthracite | Dry F.C., 98% or more (dry V.M., 2% or less) |
|  | 2. Anthracite | Dry F.C., 92% or more and less than 98% (dry V.M., 8% or less and more than 2%). |
|  | 3. Semianthracite[b] | Dry F.C., 86% or more and less than 92% (dry V.M., 14% or less and more than |

TABLE A-continued

Classification of Coals by Rank.[a]
(Legend: F.C. = fixed carbon; V.M. = volatile matter; B.t.u. = British thermal units)

| Class | Group | Limits of fixed carbon or B.t.u., ash free basis |
|---|---|---|
| | | 8% |
| | 1. Low-volatile bituminous coal | Dry F.C., 78% or more and less than 86% (dry V.M., 22% or less and more than 14%) |
| | 2. Medium-volatile bituminous coal | Dry F.C., 69% or more and less than 78% (dry V.M., 31% or less and more than 22%) |
| II. Bituminous[d] | 3. High-volatile A bituminous coal | Dry F.C., less than 69% (dry V.M. more than 31%; and moist[c] B.t.u. 14,000[e] or more |
| | 4. High-volatile B bituminous coal | Moist[c] B.t.u., 13,000 or more and less than 14,000[e] |
| | 5. High volatile C bituminous coal[f] | Moist[c] B.t.u., 11,000 or more and less than 13,000[e] |
| III. Subbituminous | 1. Subbituminous A coal | Moist B.t.u., 11,000 or more and less than 13,000[e] |
| | 2. Subbituminous B coal | Moist B.t.u. 9500 or more and less than 11,000[e] |
| | 3. Subbituminous C coal | Moist B.t.u., 8300 or more and less than 9500[e] |
| IV. Lignitic | 1. Lignite | Moist B.t.u., less than 8300 |
| | 2. Brown coal | Moist B.t.u., less than 8300 |

[a]This classification does not include a few coals that have unusual physical and chemical properties and that come within the limits of fixed carbon or B.t.u. of the high-volatile bituminous and subbituminous ranks. All of these coals either contain less than 48% moisture and ash free fixed carbon or have more than 15,500 moist, ash free B.t.u.
[b]If agglomerating, classify in low volatile group of the bituminous class.
[c]Moist B.t.u. refers to coal containing its natural bed moisture but not including visible water on the surface of the coal.
[d]It is recognized that there may be noncaking varieties in each group of the bituminous class.
[e]Coals having 69% or more fixed carbon on the dry, mineral-matter-free basis shall be classified according to fixed carbon, regardless of B.t.u.
[f]There are three varieties of coal in the high-volatile C bituminous coal group, namely, Variety 1, agglomerating and nonweathering; Variety 2, agglomerating and weathering; Variety 3, nonagglomerating and nonweathering.
Source: A.S.T.M. D388-38 (ref. 1).

As can be seen from Table 1 above, the preferred coals according to the present invention comprise the lowest ranked coals, the non-agglomerating, subbituminous and lignitic classes, III and IV.

For purposes of definition, the non-oxidizing conditions as used to describe and claim the invention refers to any condition of mining, transportation, storage, drying and reacting the coals, especially the preferred coals employed according to the invention, that allows for between 80 to about 99 per cent especially about 90 to about 99 per cent and preferably about 95 to about 99 per cent of maximum production of phenolic compounds, employing the other ennumerated and claimed reaction conditions according to this invention. Maximum recovery or manufacture of phenolic compounds employing the reaction conditions of the present invention is based on the phenolics recovered from the coal especially the preferred coals of the present invention which are at no times exposed or substantially exposed to any air or other oxidation conditions prior to hydrocarbonization.

The coal employed in the process of this invention can be any coal which is non-agglomerating under the process conditions, such as the lignites, subbituminous C coals and the like. Preferred coals are those containing at least 15 per cent oxygen, and preferably 18 to 25 per cent oxygen, on an MAF basis. The coal size can be about 10 mesh or less, with particle sizes of from about 20 to about 200 mesh being preferred.

The coal, when it is fed into the hydrocarbonization zone, is rapidly hydrocarbonized, leaving a solid particulate char in the bed, which is then withdrawn from the bed. The coal is fed at a rate such that the average solid residence time in the hydrocarbonization zone is from about 1 to 30 minutes, preferably 3 to 12 minutes.

As indicated above, it is the object of this invention to maximize the amount of liquid products, particularly phenolic compounds, including phenols, cresols, xylenols, ethyl phenols and the like in proportion to the amount of hydrogen consumed. It has been discovered by this invention that, to obtain this objective, not only must the process conditions be maintained within the limits set forth above, they also depend upon each other.

This interdependence of process conditions results because of the effect of each variable on product yields and hydrogen consumed. For example, the yield of tar increases with increasing time, but tends to level off at a limit, which is dependent on temperature, above which there is little or no increase in tar yield. This limit is about 10 minutes at about 540° C., but decreases to as low as 8 minutes at 570° C. On the other hand, the amount of hydrogen consumed increases continuously with increasing residence time. Both the yield of tar and the amount of hydrogen consumed increase with increasing hydrogen pressure, with the amount of hydrogen consumed increasing proportionately faster.

The variable having the greatest effect on tar and phenolic yield per unit of hydrogen consumed is temperature. In general, the yield of tar increases slowly with temperature to a maximum, and then decreases because of the hydrocracking of tar components to uncondensable gases. On the other hand, the amount of hydrogen consumed increases very rapidly with temperature. In addition, the amount of oxygen in the char decreases with temperature and, once the char is depleted of oxygen, further reaction of char and hydrogen will not produce the desired phenolic products. As a result, the yield of tar and phenols per unit of hydrogen consumed increases with temperature to a well-defined maximum and then rapidly decreases.

Accordingly, to maximize the yield of phenols and tar per unit of hydrogen consumed, the process variables must conform to the relationship defined by the equation:

$$(I) \quad S_H = T(P)^{0.067} (t)^{0.067}$$

wherein $S_H$ is the hydrocarbonization severity factor having a value of from 530 to 640, preferably from 560 to 630; T is the average hydrocarbonization temperature in ° C.; P is the log mean average hydrogen partial pressure in psi divided by 1000; and t is the solids residence time in minutes. When this relationship is observed, the weight ratio of phenolic compounds boiling below 230° C. to hydrogen consumed will generally be about 3.5 to about 4 or higher.

Many products produced by the hydrocarbonization of coal in accordance with this invention are cresols and other substituted phenols which may desirably be dealkylated to form phenol. Although the dealkylation can be accomplished in a step separate from the hydrocarbonization, it has been found by this invention that, if the vapors produced by the hydrocarbonization are retained in the fluidized bed for from about 10 seconds to about 250 seconds, preferably from about 30 to about 150 seconds, considerable dealkylation of the substituted phenols occurs. It has been further found that the presence of the char in the fluidized bed acts as a catalyst for the dealkylation, permitting a degree of dealkylation equivalent to that obtained at higher temperatures in the absence of the char.

For optimum results from this dealkylation step, it has been found that the temperature and vapor residence time must conform to the following equation:

$$(II) \quad S_c = T (\theta)^{0.048}$$

wherein $S_c$ is a cracking severity factor having a value of from 640 to about 750, preferably 650 to 710; T is the temperature in ° C.; and $\theta$ is the vapor residence time in seconds.

The product gas comprises vapor products from the hydrocarbonization and consists mainly of gaseous products such as water, carbon dioxide, carbon monoxide, methane and the like, as well as unreacted hydrogen, and a condensable "tar" fraction. The tar fraction can be readily distilled to recover valuable chemicals, including phenols. The tar contains a sizeable quantity of material boiling at temperatures in excess of about 230° C. which is useful mainly as a fuel. It has been found by this invention, however, that this high boiling material can be recycled to the hydrocarbonization zone to be hydrocracked to compounds boiling below 230° C., thereby permitting substantially all of the vapor products produced by the hydrocarbonization to be recovered as valuable, low-boiling chemicals. The high-boiling material is fed to the hydrocarbonization zone at a point sufficient to permit conversion of about 25 to 40 per cent of the recycled materials to products boiling below about 230° C. In this manner the over-all yield of low boiling phenolic materials is increased and the ratio of phenols produced to hydrogen consumed is also increased. Because this material will flash vaporize when fed to the hydrocarbonization zone, the hydrocarbonization is still conducted in the dry phase. By this modification, the three process steps of hydrocarbonization, dealkylation of substituted phenols, and a secondary hydrocracking of coal tars are conducted simultaneously.

The char produced by the hydrocarbonization process of this invention is very reactive and contains fairly large quantities of hydrogen, generally about 4 weight per cent on an MAF basis. It has been found that if the char is heated to a temperature of 800° to 900° C., preferably 840° to 880° C., one can obtain a gas stream containing about 75 to 85 volume per cent hydrogen, with the balance comprising mainly carbon monoxide. This hydrogen stream, after removal of the contaminants, can be employed as the fluidizing gas, thereby substantially lessening the requirement for hydrogen from some other source. It is preferred that this "calcination" process be conducted in a fluidized bed, employing, for example, steam as the fluidizing medium. The pressure is preferably atmospheric. The solids residence time in the calcination zone can vary from about 2 to about 10 minutes, and is preferably from about 3 to about 7 minutes.

The following examples are illustrative.

EXAMPLES 1–19

The apparatus employed in these examples is shown schematically in the drawing, and consisted essentially of coal hopper 1 having a 3500-gram capacity constructed from a 3-inch diameter by 4-foot high schedule 80 carbon steel pipe; reactor 3 comprising reaction zone 5 constructed from a 1-inch I.D. by 9-inch high stainless steel tube having a ¼ inch wall thickness and expanded head 7 constructed from a 2-inch diameter by 18-inch high schedule 80 pipe; steam-cooled condenser 9; two water-cooled condensers 11 and 13; and gas recycle compressor, not shown. To ensure removal of condensibles from the vapor stream, the system also employed either solvent scrubber 15 or activated carbon trap 17. Reactor 3 was equipped with an axially-mounted thermowell, not shown, containing four thermocouples located 1, 4, 7 and 12 inches from the bottom of reactor 3.

In operation, hopper 1 is charged with a weighed amount of 40–100 mesh subbituminous C coal which was mined and immediately stored under water. The coal is brought to the reactor and dewatered and dried under non-oxidizing conditions. The system is purged of air, reactor 3 is heated to about the desired reaction condition and gas flows and pressures are established. Hydrogen from gas cylinders is employed as the gas phase. When the desired temperature, pressure and gas flow rates are established, the coal feed is begun and continued until the hopper is empty, at which time the system is shut down and cooled. During the run, char is removed from reactor 3 through overflow line 19 and collected in char receiver 21, and tars and water are allowed to accumulate in condensers 9, 11 and 13 and scrubber 15, if employed.

On the termination of the run, the char receiver is emptied and the char is weighed. The condensers are drained into a common receiver 23 and the product is filtered, with the filter cake being added to the char for purposes of determining yields. The filtrate is then stripped to remove solvent, if present, and water, to a kettle temperature of 200° C. at atmospheric pressure. Any light oil which distilled off with the water is separated from the distillate by decantation and returned to the still. The tar is then distilled to recover four fractions: (1) a first fraction boiling below 130° C. at atmospheric pressure and a reflux ratio of 3 to 1; (2) a second fraction, or "light oil", boiling at 130° C. to 260° C. at 50 mm. and a reflux ratio of 6 to 1; (3) a third fraction, or "middle oil," boiling at 260° to 340° C. at 10 mm. and a reflux ration of 3 to 1; and (4) a residue consisting of pasting oil (boiling at 340° C. to 350° C. at 10 mm.) and pitch.

Tar fractions are analyzed by titration or gas chromatographic analysis for the presence of phenolic materials or "tar acids."

The data for these experiments are summarized in tabular form below:

Example Nos. 1–19

| Example | 1 | 2 | 3 | 4 | 5 | 6 | 7 | 8 | 9 |
|---|---|---|---|---|---|---|---|---|---|
| Coal | | | | | | | | | |
| Ultimate Analysis[1] | | | | | | | | | |
| C | 72.2 | 72.5 | 72.6 | 72.3 | 73.2 | 70.6 | 73.2 | 73.0 | 71.0 |
| H | 5.2 | 5.5 | 5.1 | 5.2 | 5.5 | 5.1 | 5.5 | 5.3 | 5.1 |
| N | 1.0 | 1.4 | 1.6 | 1.7 | 2.0 | 1.4 | 1.3 | 1.0 | 2.1 |
| S | 0.8 | 1.0 | 1.0 | 1.2 | 1.2 | 1.0 | 0.8 | 0.9 | 1.0 |
| O | 20.8 | 19.6 | 19.7 | 19.6 | 18.1 | 21.9 | 19.2 | 19.8 | 20.8 |
| Ash[2] | 11.5 | 16.6 | 10.5 | 18.1 | 18.0 | 14.0 | 13.8 | 9.0 | 15.4 |
| Reaction Conditions | | | | | | | | | |
| Temperature, ° C. | 560 | 497 | 562 | 511 | 508 | 539 | 522 | 511 | 540 |
| Pressure | | | | | | | | | |
| Total, psig | 340 | 1000 | 650 | 1000 | 1000 | 500 | 1000 | 1000 | 1000 |
| Hydrogen, psi[3] | 300 | 940 | 600 | 920 | 910 | 450 | 860 | 956 | 890 |
| Solids residence time, minutes | 3.8 | 8.7 | 2.8 | 8.2 | 8.8 | 8.4 | 7.4 | 9.4 | 4.9 |
| Total time, hr. | 3.5 | 8.17 | 2.5 | 7.83 | 8.67 | 8.33 | 6.42 | 8.42 | 4.67 |
| $S_H$ | 564 | 572 | 581 | 583 | 585 | 590 | 591 | 592 | 596 |

| Example | 10 | 11 | 12 | 13 | 14 | 15 | 16 | 17 | 18 | 19 |
|---|---|---|---|---|---|---|---|---|---|---|
| Coal | | | | | | | | | | |
| Ultimate Analysis[1] | | | | | | | | | | |
| C | 71.5 | 71.4 | 71.0 | 73.5 | 71.0 | 70.9 | 70.8 | 73.5 | 72. | 72.1 |
| H | 5.3 | 5.0 | 5.0 | 5.2 | 5.1 | 5.2 | 5.2 | 5.3 | 5.3 | 5.3 |
| N | 1.1 | 1.8 | 1.7 | 1.9 | 1.3 | 1.4 | 1.4 | 1.0 | 1.4 | 1.3 |
| S | 0.8 | 1.0 | 1.0 | 1.2 | 1.2 | 1.1 | 1.1 | 0.9 | 1.0 | 1.0 |
| O | 21.3 | 20.8 | 21.3 | 18.2 | 21.4 | 21.4 | 21.5 | 19.3 | 20.3 | 20.4 |
| Ash | 10.8 | 17.1 | 16.8 | 12.0 | 16.2 | 15.9 | 15.6 | 9.3 | 16.0 | 9.5 |
| Reaction Conditions | | | | | | | | | | |
| Temperature, ° C. | 560 | 571 | 538 | 558 | 536 | 536 | 536 | 543 | 567 | 567 |
| Pressure | | | | | | | | | | |
| Total, psig | 340 | 1000 | 750 | 340 | 1000 | 1000 | 1000 | 1000 | 1000 | 1000 |
| Hydrogen, psi[3] | 310 | 830 | 667 | 320 | 890 | 895 | 900 | 945 | 875 | 936 |
| Solids residence time, minutes | 8.2 | 2.9 | 9.8 | 12.5 | 9.5 | 10 | 10.6 | 9.2 | 9.0 | 10.2 |
| Total time, hr. | 7.42 | 2.67 | 9.62 | 10.75 | 9.33 | 19.24 | 9.92 | 8.67 | 8.5 | 9.25 |
| $S_H$ | 597 | 606 | 610 | 611 | 620 | 621 | 623 | 627 | 650 | 661 |

| Results | 1 | 2 | 3 | 4 | 5 | 6 | 7 | 8 | 9 |
|---|---|---|---|---|---|---|---|---|---|
| Product Yields | | | | | | | | | |
| Wt. % MAF Coal | | | | | | | | | |
| Char | 58.2 | 49.5 | 54.2 | 44.0 | 44.6 | 48.4 | 35.8 | 50.7 | 45.0 |
| Tar | 15.3 | 23.4 | 17.0 | 27.6 | 25.4 | 19.5 | 28.0 | 22.3 | 25.6 |
| Gas | 12.0 | 13.0 | 11.9 | 18.5 | 19.9 | 16.5 | 19.9 | 14.9 | 18.0 |
| Water | 15.6 | 13.6 | 18.0 | 14.7 | 13.5 | 15.6 | 18.3 | 12.8 | 15.3 |
| Ultimate Analyses - MAF | | | | | | | | | |
| C | 87.3 | — | 89.0 | 89.2 | 89.1 | 94.0 | 92.0 | 88.1 | 90.2 |
| H | 3.7 | — | 3.8 | 4.5 | 4.3 | 4.3 | 4.5 | 4.1 | 4.2 |
| N | 1.4 | — | 1.3 | 1.3 | 1.3 | 1.7 | 1.2 | 1.3 | 1.5 |
| S | 1.0 | — | 1.0 | 1.3 | 1.1 | 1.1 | 0.7 | 0.6 | 1.1 |
| O | 6.6 | — | 4.9 | 3.7 | 4.2 | (−1.1) | 1.6 | 5.9 | 3.0 |
| Tar Acids, wt. % MAF Coal | | | | | | | | | |
| 0–260° C. | 4.5 | — | 4.7 | 5.8 | — | 4.4 | — | 5.0 | — |
| 260–340° C. | 0.9 | — | 1.5 | 1.6 | — | 1.1 | — | 1.7 | — |
| Total | 5.4 | — | 6.2 | 7.4 | — | 5.5 | — | 6.7 | — |
| Hydrogen consumed, wt. % MAF Coal | 1.1 | 1.9 | 1.2 | 2.1 | 2.2 | 1.9 | 2.2 | 1.8 | 2.4 |
| Tar/H$_2$ ratio | 13.9 | 12.3 | 14.2 | 13.1 | 11.5 | 10.3 | 12.7 | 12.4 | 10.6 |
| Tar Acid/H$_2$ ratio | 4.9 | — | 5.2 | 3.5 | — | 2.9 | — | 3.7 | — |

| Results | 10 | 11 | 12 | 13 | 14 | 15 | 16 | 17 | 18 | 19 |
|---|---|---|---|---|---|---|---|---|---|---|
| Product Yields | | | | | | | | | | |
| Wt. % MAF Coal | | | | | | | | | | |
| Char | 50.4 | 44.1 | 40.2 | 50.3 | 39.6 | 38.5 | 37.5 | 39.8 | 33.3 | 38.4 |
| Tar | 21.3 | 20.8 | 25.3 | 21.0 | 27.8 | 28.4 | 29.1 | 27.3 | 27.3 | 29.0 |
| Gas | 13.7 | 19.5 | 17.5 | 13.7 | 22.5 | 21.8 | 21.0 | 17.9 | 21.7 | 19.2 |
| Water | 16.0 | 16.7 | 16.7 | 16.5 | 16.6 | 15.8 | 15.0 | 15.2 | 19.3 | 16.2 |
| Ultimate Analyses - MAF | | | | | | | | | | |
| C | 90.1 | 91.2 | 91.8 | 90.5 | 92.5 | 93.0 | 93.5 | 92.0 | 94.0 | 93.0 |
| H | 3.9 | 3.9 | 4.3 | 3.8 | 4.1 | 4.2 | 4.2 | 4.0 | 3.7 | 3.8 |
| N | 1.2 | 1.3 | 1.4 | 1.5 | 1.6 | 1.4 | 1.2 | 1.3 | 1.1 | 1.3 |
| S | 1.0 | 1.3 | 1.4 | 0.7 | 1.3 | 1.2 | 1.1 | 0.6 | 1.2 | 0.6 |
| O | 3.8 | 2.3 | 1.1 | 3.5 | 0.5 | 0.2 | 0.0 | 2.1 | 0.0 | 1.3 |
| Tar Acids, wt. % MAF Coal | | | | | | | | | | |

Example Nos. 1-19-continued

| | | | | | | | | | |
|---|---|---|---|---|---|---|---|---|---|
| 0-260° C. | 5.1 | — | 4.4 | 5.5 | — | 5.7 | — | 6.3 | — | 7.6 |
| 260-340° C. | 1.5 | — | 1.9 | 1.5 | — | 1.4 | — | 0.8 | — | 0.8 |
| Total | 6.6 | — | 6.3 | 7.0 | — | 7.1 | — | 7.1 | — | 8.4 |
| Hydrogen consumed, wt. % MAF Coal | 1.4 | 2.8 | 2.5 | 1.5 | 3.3 | 3.4 | 3.5 | 2.9 | 4.1 | 3.5 |
| Tar/H$_2$ ratio | 15.2 | 7.4 | 10.1 | 14.0 | 8.4 | 8.4 | 8.3 | 9.4 | 6.8 | 9.4 |
| Tar Acid/H$_2$ ratio | 4.7 | — | 2.5 | 4.7 | — | 2.1 | — | 2.4 | — | 2.4 |

[1] Moisture and ash free basis (MAF).
[2] Moisture free basis.
[3] partial pressure

EXAMPLES 20 and 21

Two additional runs are conducted employing apparatus and procedures similar to those employed in Examples 1-19, except that the product gas is not recycled to the reactor. These additional runs are conducted to determine the effect of the carbon dioxide present in the recycle gas on hydrogen consumption. The data for these runs are summarized below.

| Example | 20 | 21 |
|---|---|---|
| Coal | | |
| Ultimate Analysis, MAF | | |
| C | 73.7 | 73.0 |
| H | 5.1 | 5.1 |
| N | 1.0 | 1.3 |
| S | 1.0 | 1.0 |
| O | 19.2 | 19.6 |
| Ash, moisture free | 8.5 | 8.5 |
| Reaction Conditions | | |
| Temperature, ° C. | 544 | 531 |
| Pressure | | |
| Total, psig. | 600 | 600 |
| Hydrogen, psi.(partial pressure) | 600 | 600 |
| Solids residence time, minutes | 13.2 | 14.8 |
| Total time hr. | 12.4 | 11.3 |
| $S_H$ | 624 | 615 |
| Results | | |
| Product Yields | | |
| Wt. % MAF coal | | |
| Char | 45.6 | 48.5 |
| Tar | 23.6 | 25.2 |
| Gas | 16.0 | 14.2 |
| Water | 16.8 | 13.7 |
| Char-Ultimate Analysis, MAF | | |
| C | 90.5 | 90.4 |
| H | 3.9 | 4.1 |
| N | 1.2 | 1.2 |
| S | 0.9 | 0.9 |
| O | 3.5 | 3.4 |
| Tar Acids, % MAF Coal | | |
| 0-260° C. | 6.3 | 6.1 |
| 260-340° C. | 1.3 | 1.5 |
| Total | 7.6 | 7.6 |
| Hydrogen consumed, % MAF Coal | 2.0 | 1.6 |
| Tar/H$_2$ ratio | 11.8 | 15.8 |
| Tar acid/H$_2$ ratio | 3.8 | 4.75 |

By comparison of the amounts of hydrogen consumed and tar and tar acids produced per unit hydrogen consumed in these examples with those runs employing recycle having similar severity factors ($S_H$) it can be seen that improved results are obtained when no gas recycle is employed. Thus, at a severity factor of 624 without recycle (Example 20) the amount of hydrogen consumed in only 2.0 per cent of the coal, as compared with 2.9 to 3.5 for Examples 16 and 17. In addition, the ratios of tar and tar acids to hydrogen consumed is 11.8 and 3.8, respectively, in Example 20. In contrast, the tar to hydrogen ratios in Examples 16 and 17 is only 8.3 to 9.4, and the tar acid to hydrogen ratio of Example 17 was only 2.4.

These improved results are due to the avoidance of the following reactions.

$$H_2 + CO_2 \rightarrow H_2O + CO$$

$$3H_2 + CO \rightarrow CH_4 + H_2O$$

because of the presence of carbon dioxide or monoxide in the system in significant amounts due to recycle.

EXAMPLE 22

Employing techniques similar to those employed in the preceding examples, a pilot-plant run is made over about one week. The reactor in this run is 11 inches in diameter and 20 feet high. The hydrocarbonization temperature is 540° C., the hydrogen partial pressure is 397 psi and the solids residence time is 14.3 minutes, for a hydrocarbonization severity factor ($S_H$) of 606.

The product yields, based on MAF coal, are 53 per cent char, 19 per cent tar, 15.5 per cent gas and 15.2 per cent water at a hydrogen consumption of 1.74 per cent based on MAF coal. Tar acids boiling below 230° C. amounted to 5.60 per cent of MAF coal. Thus, the ratio of tar to hydrogen consumed is 10.9 and the ratio of tar acids boiling below 230° C. to hydrogen consumed is 3.22.

On recycle of tar boiling above 230° C., the yield of tar acids boiling below 230° C. is increased from 5.61 per cent to 7.04 per cent of MAF coal at a total hydrogen consumption of 1.93 per cent of MAF coal, for a low temperature tar acid to hydrogen ratio of 3.65 as compared to 3.22 without recycle.

The data of this example, when compared with that of Example 12 also indicates the effect of simultaneous dealkylation of alkylphenols on product distribution. The vapor residence time in the small reactor of the previous examples is too short to permit the occurrence of significant dealkylation. In this example, however, the vapor residence time is 18.5 seconds, for a severity factor ($S_c$) of only 640, which is below the preferred range. Nevertheless, the proportion of tar acids boiling below 260° C. to all tar acids boiling below 340° C. increased from 70 per cent in Example 12 to over 81 per cent in this example.

The coal employed in several of the following experiments is generally known as Lake DeSmet coal. This coal is taken from an unusual formation in Northern Wyoming and exists in the form of lens of coal with thicknesses up to 200 feet. This deposit of coal lies near the surface of the ground, and in time past has partially burned out forming a basin now filledwith water. This is known as Lake De Smet. The coal employed was taken from the land next adjacent to the Southern border of the lake. The coal is of subbituminous C rank.

It has been found in one aspect of the present invention that even mild exposure of the low rank Lake DeSmet coal to air oxidation results in a marked decrease in process yields of phenolic compounds. For example, drying the coal in a commercial vacuum oven at 50° C. and grinding and screening the dried coal in air reduces the tar yield by about 50 per cent with a proportionate loss of phenolic compounds.

EXAMPLE 23

Hydrocarbonization of Lake De Smet Coal

In the hydrocarbonization of Lake de Smet coal, it is found that extreme care is necessary in order to prevent oxidation and obtain truly representative yields from this low-rank coal.

A sample of Lake de Smet coal is carefully protected for shipment by placing the wet cores in polyethylene bags and surrounding the bags as they were packed in a box with wet core cuttings. On arrival at the research laboratory, an aliquot sample of the cores is picked, partially dried at ambient temperature in a vacuum desiccator, ground and analyzed. The balance of the core samples is placed in a commercial vacuum drying oven and dried overnight at 50° C. The cores are then ground to yield sufficient 40–100 mesh coal for two experimental runs. The hydrocarbonization unit and the operating procedure employed in this and in all succeeding experiments in this report are described in Examples 1–19.

The analysis of the aliquot sample and the sample prepared for experimental use are shown in Table I. The operating conditions and the product yields are shown in Table II.

TABLE I

PROPERTIES OF LAKE DE SMET COAL

| Proximate Analysis | Aliquot Sample Weight Per Cent as Received | Experimental Sample |
|---|---|---|
| Volatile Matter | 33.8 | 38.2 |
| Fixed Carbon | 35.8 | 45.9 |
| Moisture | 19.3 | 1.5 |
| Ash | 11.1 | 14.4 |
| Ultimate Analysis, Weight Per Cent MAF | | |
| C | 72.4 | 72.2 |
| H | 5.3 | 4.3 |
| N | 1.6 | 1.5 |
| S | 1.6 | 1.7 |
| O (by difference) | 19.1 | 20.3 |

TABLE II

CARBONIZATION AND HYDROCARBONIZATION OF LAKE DE SMET COAL

| | Operating Conditions | | |
|---|---|---|---|
| | Col. (1) Experimental Sample | Col. (2) Experimental Sample | Col. (3) Non-Oxidized Non-Air Dried Lake De Smet Coal |
| Fluidization Gas | Nitrogen | Hydrogen | Hydrogen |
| Pressure, psig. | 200 | 400 | 500 |
| Temperature, °C. | 515 | 515 | 539 |
| Hydrogen Partial Pressure, psi. | nil | 320 | 450 |
| | Yield, Weight Per Cent MAF Coal | | |
| Char | 76.6 | 68.9 | 48.4 |
| Tar | 5.9 | 8.9 | 19.5 |
| Gas | 9.0 | 11.6 | 16.5 |
| Water | 8.5 | 11.5 | 15.6 |
| Hydrogen | — | −0.9 | −1.9 |
| | 100.0 | 100.0 | 100.0 |

Discussion of Results

The yield of tar from the experimental supply of Lake de Smet coal is only 5.9 per cent MAF coal when car-bonized in an inert atmosphere as shown in Column 1, Table 2. The char yield is 76.6 per cent. Furthermore, Column 2 shows that in a hydrogen atmosphere, at a hydrogen partial pressure of 320 psi., the tar yield increases to only 8.9 per cent. Interpolation of data shown in column 3 obtained from unoxidized coal in succeeding runs at the same operating conditions, shows that the tar yield should be about 17.0 per cent and 57.07% char. The char yield is 68.9. Turning to the ultimate analyses given in Table I, it is apparent that the experimental supply of coal lost hydrogen, down from 5.3 to 4.3 per cent and gained oxygen, up from 19.1 to 20.3 per cent during the drying and grinding operations. The adverse effect of oxidation on the tar yields from these experiments shows that extreme care is required in handling the coal in order to obtain maximum yields of phenolics.

EXAMPLE 24

Drying in the Presence of Oxygen

Combustion processes to produce hot flue gases usually are run with an excess of oxygen (air) to ensure complete combustion of the fuel. In the tentative design for a commercial hydrocarbonization plant, hot flue gas containing 2 per cent free oxygen is used to dry and preheat the pulverized coal. Two separate fluidized vessels are used, a dryer operating at 100° C. and a preheater operating at 285° C. A study is made to define the effect of using a flue gas containing 2 per cent oxygen in drying and preheating coal upon the tar yield during subsequent hydrocarbonization. The method chosen to evaluate the tar yield of the treated coal is the Fischer Assay test. (U.S. Bureau of Mines Bulletin 530, 1953, "Low Temperature Carbonization Assay of Coal in a Precision Laboratory Apparatus," by Goodman, J. B., Gomez, M., Parry, V. F., and Landers, W. S.).

1. Preparation of Samples

The Lake De Smet coal in this example is taken from a 55-gallon drum in which the coal had been covered with water from the time it had been shipped. The wet lump coal is surface dried, pulverized, screened to obtain a 40–100-mesh fraction, and stored under positive pressure nitrogen until ready for use. A moisture determination of 29.5 percent shows that this coal has been little more than surface dried during preparation, since the moisture content of coal as mined is approximately 30 percent. A 3-quart sample of this prepared coal is put in a 1-gallon metal sample can, flushed with nitrogen, and the lid soldered on. This sample (No. 1) is used to establish the base yield of tar by the Fischer The results of this study show that the Lake de Smet coal is sensitive to as little as 2 per cent oxygen in the gas used for drying and preheating the coal.

Table III

| Sample | PRECISION LABORATORY CARBONIZATION ASSAYS AND ANALYSES UNION CARBIDE DE SMET COAL SAMPLES | | | | | | | |
|---|---|---|---|---|---|---|---|---|
| | 1 | 1 | 2 | 2 | 3 | 3 | 4 | 4 |
| Temp. of Carbonization, °C. | 500 | 500 | 500 | 500 | 500 | 500 | 500 | 500 |
| Carbonization Yields, MAF % | | | | | | | | |
| Char | 67.6 | 67.5 | 66.3 | 66.2 | 66.4 | 66.4 | 67.7 | 67.9 |
| Water formed | 10.3 | 10.4 | 11.6 | 11.6 | 12.0 | 12.1 | 11.2 | 11.1 |
| Tar, Dry | 9.3 | 9.3 | 9.3 | 9.2 | 8.8 | 8.5 | 7.7 | 8.0 |
| Light Oil | 1.1 | 1.1 | 1.1 | 0.9 | 0.9 | 0.9 | 1.0 | 0.9 |
| Gas | 11.5 | 11.5 | 11.4 | 12.1 | 11.6 | 11.8 | 12.0 | 11.8 |
| Hydrogen Sulfide | 0.3 | 0.3 | 0.2 | 0.2 | 0.3 | 0.3 | 0.3 | 0.3 |
| Total | 100.1 | 100.1 | 99.9 | 100.2 | 100.0 | 100.0 | 99.9 | 100.0 |

Notes
Sample
1. Raw Lake de Smet coal; sample contains 29.6 per cent moisture (xylol method) and 6.1 per cent ash.
2. Dried Lake de Smet coal; sample dried at 100° C.; fluidization gas: nitrogen. Sample contains 5.8 per cent moisture (xylol) and 8.2 per cent ash.
3. Dried Lake de Smet coal; sample dried at 100° C.; fluidization gas: 2 per cent oxygen and 98 per cent nitrogen. Sample contains 4.4 per cent moisture (xylol) and 8.8 per cent ash.
4. Dried Lake de Smet coal; sample dried at 285° C.; fluidization gas: 2 per cent oxygen and 98 per cent nitrogen. Sample contains 1.1 per cent moisture (xylol) and 8.6 per cent ash.

Assay. The other samples, Nos. 2, 3, and 4 are prepared in the aforementioned hydrocarbonization unit previously described in Examples 1–19. The pertinent operating conditions used to prepare Samples 2, 3, and 4 are as follows:

| | Samples | | |
|---|---|---|---|
| | 2 | 3 | 4 |
| Drying Temperature, °C. | 100 | 100 | 285 |
| Coal Feed Rate, g/Hr. | 250 | 250 | 580 |
| Residence Time, min. | 15 | 15 | 7 |
| Fluidization Gas | High Purity Nitrogen | 98% Nitrogen 2% Oxygen | 98% Nitrogen 2% Oxygen |
| Gas Flow, SCFH | 5.6 | 5.6 | 5.6 |
| Weight Percent Oxygen Relative to Coal | 0 | 1.7 | 0.7 |

The coal receiver is allowed to cool to room temperature under a positive pressure of high purity nitrogen. The cold samples are then assayed by the Fischer Assay test.

Fischer Assay Results

The complete assay results are given in Table III. The pertinent assay results are summarized as follows:

| | Sample Numbers | | | |
|---|---|---|---|---|
| | 1 | 2 | 3 | 4 |
| Char Yield, % MAF | 67.6 | 66.3 | 66.4 | 67.8 |
| Tar and Light Oil, % MAF | 10.4 | 10.3 | 9.6 | 8.8 |
| % Loss in Tar Yield | — | 1.0 | 7.7 | 15.4 |

EXAMPLE 25

Hydrocarbonization yields are determined for samples of Wyodak coal (a subbituminous C coal from a strip mine near Gillette, Wyo.) and Texas and North Dakota lignites. The results are compared to the results obtained from Lake de Smet coal at similar operating conditions.

The experimental apparatus and the operating procedure are the same as used in Examples 1–19 and additionally, air oxidation of the coal and lignite is also avoided.

Experiments are made to determine the hydrocarbonization yields from Wyodak coal and Texas and North Dakota lignites at 1000 psig, 510°–535° C. and a residence time of 8 to 10 minutes. For comparison, the hydrocarbonization yields for Lake de Smet coal, at similar operating conditions, are presented.

The analyses of the feed coals and lignites and the hydrocarbonized chars are given in Table IV. The operating conditions, yields and hydrogen consumption are given in Table V. Table VI gives the gas yields and composition. The physical properties of the tars are given in Table VII.

TABLE IV

| ANSLYSES OF FEED COAL AND LIGNITES AND HYDROCARBONIZED CHAR | | | | |
|---|---|---|---|---|
| Coal or Lignite | Lake de Smet | Texas Lignite | North Dakota Lignite | Wyodak Coal |
| | Ultimate Analysis, Weight Per Cent MAF Feed | | | |
| Element | | | | |
| C | 72.3 | 74.8 | 72.0 | 73.8 |
| H | 5.2 | 5.7 | 5.0 | 5.3 |
| N | 1.7 | 1.6 | 1.0 | 1.0 |
| S | 1.2 | 1.6 | 1.1 | 0.6 |
| O (by difference) | 19.6 | 16.3 | 20.9 | 19.3 |
| % Ash, dry basis | 18.1 | 11.6 | 7.6 | 5.8 |

TABLE IV-continued

ANSLYSES OF FEED COAL AND LIGNITES AND HYDROCARBONIZED CHAR

| Coal or Lignite | Lake de Smet | Texas Lignite | North Dakota Lignite | Wyodak Coal |
|---|---|---|---|---|
| | | Hydrocarbonized Char | | |
| C | 89.2 | 87.5 | 88.6 | 89.0 |
| H | 4.5 | 4.2 | 4.1 | 4.0 |
| N | 1.3 | 2.0 | 1.3 | 1.3 |
| S | 1.3 | 1.6 | 0.8 | 0.6 |
| O(by difference) | 3.7 | 4.7 | 5.2 | 5.1 |

TABLE V

HYDROCARBONIZATION OF LIGNITES AND WYODAK COAL OPERATING CONDITIONS AND YIELDS

| | Operating Conditions | | | |
|---|---|---|---|---|
| Coal or Lignite | Lake de Smet | Texas Lignite | N.D. Lignite | Wyodak |
| Hydrocarbonization Temperature, °C. | 511 | 512 | 510 | 535 |
| System Pressure, psig. | 1000 | 1000 | 1000 | 1000 |
| Fluidization Gas | Hydrogen | Hydrogen | Hydrogen | Hydrogen |
| Avg. $H_2$ Partial Pressure, psi. | 920 | 890 | 900 | 920 |
| Residence Time (defined time required to fill the carbonizer with fresh feed at 30 lbs./ft. 3 fluidized density), minutes | 8.2 | 8.1 | 9.8 | 9.8 |
| Length of Run, hrs. | 7.83 | 6.58 | 7.92 | 8.42 |
| | Yields, Weight Per Cent MAF Feed | | | |
| Char | 44.0 | 43.0* | 48.3 | 48.1 |
| Tar | 27.6 | 31.2 | 27.0 | 26.9 |
| Gas | 18.5 | 18.7 | 14.7 | 15.3** |
| Water | 14.7 | 9.6 | 15.1 | 11.7 |
| Hydrogen | −2.1 | −2.5 | −2.3 | −2.0 |
| Unaccounted for | −2.7 | 0.0 | −2.8 | 0.0 |
| | 100.0 | 100.0 | 100.0 | 100.0 |

*An unknown amount of feed was left in hopper, yields are normalized to 100%
**Gas by difference

TABLE VI

HYDROCARBONIZATION OF LIGNITES AND WYODAK COAL GAS YIELDS AND COMPOSITION

| Coal or Lignite | Lake de Smet | Texas Lignite | N.D. Lignite | Wyodak |
|---|---|---|---|---|
| | | Gas Yields | | |
| Weight Gas, Lb./Ton MAF | 370 | 374 | 294 | 306 |
| Volume Gas, SCF/Ton MAF | 5300 | 5820 | 4570 | 4830 |
| | Gas Composition, Volume Per Cent | | | |
| Component | | | | |
| Methane | 35.7 | 45.6 | 44.0 | 48.9 |
| Ethane | 11.4 | 12.7 | 11.6 | 11.3 |
| Propane | 2.1 | 3.7 | 3.6 | 7.6 |
| Carbon Monoxide | 29.0 | 28.3 | 32.0 | 26.5 |
| Carbon Dioxide | 21.8 | 9.7 | 8.8 | 5.7 |
| Molecular Weight of Make Gas | 27.7 | 24.9 | 24.9 | 24.5 |

TABLE VII

HYDROCARBONIZATION OF LIGNITES AND WYODAK COAL SOME PHYSICAL PROPERTIES OF THE TAR

| Coal or Lignite | Lake de Smet | Texas Lignite | N.D. Lignite | Wyodak |
|---|---|---|---|---|
| | Cyclohexane Insoluble Asphalt | | | |
| Per Cent Tar | 21.0 | 21.7 | 26.8 | 17.6 |
| Per Cent MAF Coal | 5.8 | 6.8 | 7.2 | 4.6 |
| | Tar Distillation, Weight Per Cent | | | |
| Boiling Range, °C. | | | | |
| IBP – 110 | 9.3* | 1.8** | 3.5** | |
| 110 – 260 | 29.8 | 21.5 | 29.2 | |
| 260 – 320 | 10.9 | — | — | |
| 260 – 340 | — | 17.8 | 16.0 | |
| Residue | 50.0 | 55.8 | 51.3 | |
| | Oil Yields, Per Cent MAF Coal | | | |
| IBP – 110 | 2.6 | 0.6 | 1.0 | |
| 110 – 260 | 8.2 | 6.7 | 7.9 | |
| 260 – 320 | 3.0 | — | — | |
| 260 – 340 | — | 5.6 | 4.3 | |
| Total IBP – | | | | |

TABLE VII-continued

HYDROCARBONIZATION OF LIGNITES AND WYODAK COAL
SOME PHYSICAL PROPERTIES OF THE TAR

| Coal or Lignite | Lake de Smet | Texas Lignite | N.D. Lignite | Wyodak |
|---|---|---|---|---|
| 320 | 13.8 | — | — | |
| Total IBP – 340 | — | 12.9 | 13.2 | |
| Phenols and Neutral Oil Yields, % MAF Coal (By Extraction) | | | | |
| Boiling Range, °C. | | | | |
| 110 – 260 | | | | |
| Phenols | 5.8 | 3.5 | 5.7 | |
| Neutral Oil | 2.5 | 3.2 | 2.2 | |
| 260 – 320 | | | | |
| Phenols | 1.6 | — | — | |
| Neutral Oil | 1.5 | — | — | |
| 260 – 340 | | | | |
| Phenols | — | 2.4 | 2.5 | |
| Neutral Oil | — | 3.2 | 1.9 | |
| Total Phenols, 110–320 | 7.4 | — | — | |
| Total Phenols 110–340 | — | 5.9 | 8.2 | |

*Distillation in a packed column with reflux.
**Vigreaux distillation on lignite tars.

The hydrocarbonization of a sample of Texas lignite in a hydrogen atmosphere at 1000 psig and 510° C. gave a yield of 625 pounds of tar per ton of moisture and ash free lignite. This may be compared to a tar yield of 550 pounds per ton when Lake de Smet coal is hydrocarbonized at the same operating conditions. A North Dakota lignite and Wyodak coal gave about the same tar yield as the Lake de Smet coal.

The light oil phenol yield is 115 pounds per ton of MAF feed for the North Dakota lignite and the Lake de Smet coal. The light oil phenol yield for the Texas lignite is 70 pounds per ton of MAF lignite.

The results obtained with regard to preventing air oxidation of the subbituminous C coals and lignites are unexpected in view of those results obtained according to U.S. Pat. No. 3,231,486 Perry and Albright, one of the co-inventors of the subject matter of the present application as well, wherein a subbituminous B coal, Elkol coal was employed. This particular grade of coal was an agglomerating type in hydrogen and therefore was used after some weathering or oxidation in order to run this coal in hydrogen. This in turn reduced the tar yield and consequently the phenolic yield. Although the process of the aforementioned patent U.S. Pat. No. 3,231,486 is operable in all respects, it was not realized at that time that tar yields could be maximized by the expedient of mining, transportation, storage, drying, and reacting the coal in a substantially non-oxidizing atmosphere which by definition substantially excludes air-oxidation. The difference between the invention of U.S. Pat. No. 3,231,486 and the present invention can be readily determined by reference to Table VI of U.S. Pat. No. 3,231,486 teaching the production of 8.9 to 9.7 pounds of phenols per ton of coal employing methods of the prior art whereas the results obtained according to the present invention, especially Example 6, show approximately 110 pounds of tar acids per ton of coal are obtained under conditions comparable to those employed in U.S. Pat. No. 3,231,486. The tar acids of Example 6 of the present invention comprises 88 pounds of 0–260° C. phenols per ton and 22 pounds of 260°–340° C. phenols per ton. In comparing these results to Table VI of the patent, it will be seen that the phenols of Table VI of the patent are the 260° C. cut and amount to either 8.9 or 9.7 pounds per ton of coal as compared to the 88 pounds per ton of coal of the 0°–260° C. tar acids of Example 6, thus representing a nearly 900 per cent increase in phenolic yields by employing the method of the present invention.

What is claimed is:

1. A fluidized bed process for maximizing the production of phenolic compounds comprising the steps of:

a. preheating a non-agglomerating subbituminous C coal or lignitic coal in a substantially nonoxidized state to a temperature of about 250° C. to about 300° C. in a substantially non-oxidizing atmosphere;
   b. feeding said coal and a hydrogen containing oxygen-free feed gas to a hydrocarbonization zone;
   c. fluidizing said coal as a fluidized bed in said hydrocarbonization zone;
   d. reacting said coal with said hydrogen at a temperature of from about 480° C. to about 600° C. to product a product gas comprising condensable vapor products and a solid char;
   e. fluidizing said char as it is formed as a part of said fluidized bed;
   f. maintaining the solids in said hydrocarbonization zone from about 1 to about 30 minutes and said vapor from about 10 to about 250 seconds;
   g. maintaining said hydrogen in the hydrocarbonization zone at a hydrogen partial pressure of about 100 to about 1200 psi;
   h. withdrawing from said hydrocarbonization zone the said product gas and solids;
   i. condensing said condensable vapor in said product gas to obtain condensed tar fraction
   j. separating phenols from said condensed tar fraction.

2. The process as claimed in claim 1 wherein the temperature, hydrogen partial pressure and solids residence time conform to the equation:

$$S_H = T (P)^{0.067} (t)^{0.067}$$

wherein $S_H$ is a hydrocarbonization severity factor having a value of from 530 to 640; $T$ is the hydrocarbonization temperature in ° C.; $P$ is the log mean average hydrogen partial pressure in said hydrocarbonization zone in psi divided by 1000; and $t$ is the solids residence time in minutes.

3. The process as claimed in claim 2 where in order to maximize dealkylation of the phenols obtained in the presence of the char as a catalyst, the temperature and vapor residence time conform to the equation:

$$S_c = T\,(\theta)^{0.048}$$

$S_c$ is a vapor cracking severity factor having a value of from 640 to 750; T is the temperature in °C.; P is the log mean average hydrogen partial pressure in psi divided by 1000; t is the average solids residence time in minutes; and $\theta$ is the average vapor residence time in seconds.

4. The process of claim 1 where said tar fraction is separated into phenols and a fraction boiling above about 230° C. and said fraction is recycled to said hydrocarbonization zone and is hydrocracked to compounds boiling below 230° C. whereby the over-all yield of low boiling phenols, boiling below 230° C. is increased and the ratio of phenols produced to hydrogen consumed is also increased.

5. The process of claim 2 where said tar fraction is separated into phenols and a fraction boiling above about 230° C. and said fraction is recycled to said hydrocarbonization zone and is hydrocracked to compounds boiling below 230° C. whereby the over-all yield of low boiling phenols, boiling below 230° C. is increased and the ratio of phenols produced to hydrogen consumed is also increased.

6. The process of claim 3 where said tar fraction is separated into phenols and a fraction boiling above about 230° C. and said fraction is recycled to said hydrocarbonization zone and is hydrocracked to compounds boiling below 230° C. whereby the over-all yield of low boiling phenols, boiling below 230° C. is increased and the ratio of phenols produced to hydrogen consumed is also increased.

* * * * *